United States Patent [19]
Salem

[11] Patent Number: 5,882,201
[45] Date of Patent: Mar. 16, 1999

[54] DENTAL DEBRIDEMENT METHOD AND TOOL THEREFOR

[76] Inventor: George Salem, 69 Rathbun Rd., Natick, Mass. 01760

[21] Appl. No.: 786,225

[22] Filed: Jan. 21, 1997

[51] Int. Cl.$^6$ .............................. A61C 15/00; A61C 3/06
[52] U.S. Cl. ........................................... 443/216; 433/166
[58] Field of Search .................................. 433/125, 166, 433/223, 229, 141, 142, 143, 215, 216

[56] References Cited

U.S. PATENT DOCUMENTS

| | | | |
|---|---|---|---|
| 4,636,171 | 1/1987 | Martin ...................................... | 433/134 |
| 5,078,754 | 1/1992 | Jefferies et al ........................... | 51/298 |
| 5,211,560 | 5/1993 | Lowder et al. .......................... | 433/166 |
| 5,273,559 | 12/1993 | Hammar et al. ...................... | 433/166 X |
| 5,369,916 | 12/1994 | Jefferies et al. ........................ | 451/532 |

OTHER PUBLICATIONS

Consepsis® brochure 1995.
Consepsis® Scrub brochure 1995.

*Primary Examiner*—Nicholas D. Lucchesi
*Attorney, Agent, or Firm*—Hale and Dorr LLP

[57] ABSTRACT

A dental debridement tool is provided for use with a rotary dental handpiece to remove a surface contaminant from a surface of a tooth. The tool includes a shaft extending along an axis and having a proximal end and a distal end. The proximal end is sized and shaped for connection to the rotary dental handpiece. The tool also includes an operative tip being carried at the distal end of the shaft. The operative tip has a length parallel to the axis. The length is at most 8.0 millimeters and the operative tip is no wider than 4.0 millimeters at any point along the length. The operative tip is operably compressible during removal of the surface contaminant and includes an abrasive composition of matter. The abrasive composition may include polystyrene, polyethylene, polyester, acrylic, or silicone. An abrasive powder may be included in the abrasive composition. The abrasive powder may include pumice, mica, diamond, talc, aluminum oxide, tin oxide, silicone oxide, or a ceramic material. The operative tip may have a substantially cylindrical shape, may be sufficiently compressible to conform substantially to the shape of the tooth, and may be sufficiently porous to carry a disinfecting agent. The tooth surface may be an outward-facing surface of the tooth or an inward-facing surface of the tooth.

18 Claims, 4 Drawing Sheets

DENTAL DEBRIDEMENT METHOD AND TOOL THEREFOR

BACKGROUND OF THE INVENTION

The invention relates generally to dental tools and more particularly to dental tools adapted to remove a surface contaminant from a surface of a tooth.

As is known in the art, a dentist uses a rubber prophy cup while preparing a tooth for receiving permanent restorative material such as a crown. First, the dentist drills (i.e., sculpts) the tooth into a shape appropriate for receiving the restorative material. The dentist then takes an impression of the tooth. The impression is sent to a dental laboratory for fabricating the permanent restorative material.

The permanent restorative material must mate exactly with the prepared tooth. While the permanent restorative material is being fabricated at the dental laboratory, temporary restorative material is affixed to the prepared tooth. The dentist uses temporary dental cement to attach the temporary restorative material to the tooth. The temporary dental cement causes mechanical retention between the temporary restorative material and the tooth and is used while the permanent restorative material (i.e., the crown) is being constructed. Subsequently, the dentist removes the temporary restorative material, exposing pieces of the temporary dental cement and other material requiring debridement from the tooth's surface before the permanent restorative material may be applied.

The dentist carries out such debridement using a slurry and the rubber prophy cup driven by a rotary dental handpiece. The slurry is created by mixing water and flour of pumice. After dipping the rubber prophy cup into the slurry, the dentist applies the rubber prophy cup to the tooth's surface. The rubber prophy cup is rotated by the rotary dental handpiece, resulting in at least partial debridement of the tooth's surface. Next, the dentist rinses the slurry from the tooth's surface and rinses the rubber prophy cup. To apply a disinfecting agent (e.g., a chemoactive liquid, gel, or paste, or a bactericidal agent such as but not limited to: Peridex®, a 1.23% solution of chlorhexidine gluconate by Proctor & Gamble; or Concepsis® scrub by Ultradent Products Inc. of South Jordan, Utah) for disinfecting, the dentist then dips the rubber prophy cup into the disinfecting agent and applies the rubber prophy cup to the tooth's surface again. Alternatively, the disinfecting agent is applied using small cotton pellets that are soaked in the disinfecting agent and then scrubbed over the tooth's surface. Finally, the dentist rinses the tooth's surface again and permanently attaches the permanent restorative material to the tooth.

The rubber prophy cup is sufficiently non-abrasive to avoid damaging the tooth's surface. However, the rubber prophy cup typically has a large size (such as a width or diameter of 6 to 10 millimeters) that prevents the rubber prophy cup from getting between teeth and causes parts of the tooth's surface to be left undebrided and undisinfected. In particular, such parts include interdental and intracoronal cavity surfaces.

Some characteristics of the rotary dental handpiece and of connecting a tool to the handpiece are described in U.S. Pat. No. 5,211,560 to Lowder et al, which is incorporated by reference.

SUMMARY OF THE INVENTION

In accordance with one aspect of the invention, a dental tool is provided for use with a rotary dental handpiece to remove a surface contaminant from a surface of a tooth. The tool includes a shaft extending along an axis and having a proximal end and a distal end. The proximal end is sized and shaped for connection to the rotary dental handpiece. The tool also includes an operative tip being carried at the distal end of the shaft. The operative tip has a length parallel to the axis. The length is at most 8.0 millimeters and the operative tip is no wider than 4.0 millimeters at any point along the length. The operative tip is operably compressible during removal of the surface contaminant and includes an abrasive composition of matter.

With such a tool, a dentist can debride a drilled tooth surface effectively and efficiently. The drilled tooth surface appears on a drilled tooth having a vertical wall and a horizontal gingival shoulder. The length and width of the operative tip allow the dentist to place the operative tip between the drilled tooth and an adjacent tooth for simultaneous debridement of the vertical wall and the horizontal gingival shoulder. Such placement also helps prevent abrasive contact between the tool and gingival tissues surrounding the tooth, avoiding unnecessary tissue abrasion and hemorrhaging.

Implementations of this aspect of the invention may include one or more of the following features.

The abrasive composition may be sufficiently abrasive to remove dental cement from the surface of the tooth and may also be insufficiently abrasive to remove portions of the surface of the tooth during the removal of the dental cement.

Provided with the composition of matter having the abrasiveness described above, the operative tip allows the dentist to remove from the tooth surface not only dental cement but also other surface contaminants able to be removed with a less abrasive composition of matter. Such surface contaminants include mucopolysaccharides, glycoproteins, salivary fluids, bacterial matrices, dental plaque, and materia alba. At the same time, the composition of matter having the abrasiveness described above allows the dentist to remove the surface contaminants without polishing (i.e., damaging) the tooth surface. Such polishing is undesirable because a polished tooth surface would reduce retention of any restorative material (such as crowns, inlays, onlays, and veneers) subsequently placed on the tooth. In addition, because the restorative material preferably fits the tooth's shape to a 50 micron tolerance standard, any polishing or damaging of the tooth's surface can be catastrophic to such a fit.

The abrasive composition may include polystyrene, polyethylene, polyester, acrylic, or silicone. An abrasive powder may be included in the abrasive composition. The abrasive powder may include pumice, mica, diamond, talc, aluminum oxide, tin oxide, silicone oxide, or a ceramic material.

The operative tip may have an operative outer surface and the abrasive composition may be disposed on the operative outer surface.

The operative tip may have a substantially cylindrical shape and may be sufficiently porous to carry a disinfecting agent (e.g., a chemoactive liquid).

In accordance with another aspect of the invention, a dental tool is provided for use with a rotary dental handpiece to remove a surface contaminant from a surface of a tooth. The tool includes a shaft extending along an axis. The shaft has a proximal end and a distal end. The proximal end is sized and shaped for connection to the rotary dental handpiece. The tool also includes an operative tip being carried at the distal end of the shaft. The operative tip has a length parallel to the axis. The length is at most 8.0 millimeters and the operative tip is no wider than 4.0 millimeters at any point along the length. The operative tip is configured for rotation about the axis at a rotation speed being between 300 and 5,000 revolutions per minute. The operative tip includes an abrasive composition of matter. The abrasive composition is operably compressible to allow a piece of the surface contaminant being gripped by and embedded in the abrasive composition to be sheared off the surface of the tooth by the operative tip rotating at the rotation speed.

Such a tool avoids damaging the surface of the tooth. Such damage is avoided because the tool removes pieces of surface contaminant by gripping the pieces and physically knocking or shearing the pieces off.

Implementations of this aspect of the invention may include one or more of the following features. The abrasive composition may include polystyrene, polyethylene, polyester, acrylic, or silicone. An abrasive powder may be included in the abrasive composition.

In accordance with other aspects of the invention, methods are provided for debriding a surface of a tooth. Each method includes using one of the dental debridement tools described above.

Implementations of these aspects of the invention may include one or more of the following features. The tooth surface may be an outward-facing surface of the tooth or an inward-facing surface of the tooth.

BRIEF DESCRIPTION OF THE DRAWINGS

Other aspects, features, and advantages of the invention, as well as the invention itself, will become more readily apparent when read together with the following detailed description taken together with the accompanying drawings, in which.

DESCRIPTION OF THE PREFERRED EMBODIMENTS

Figure 1:
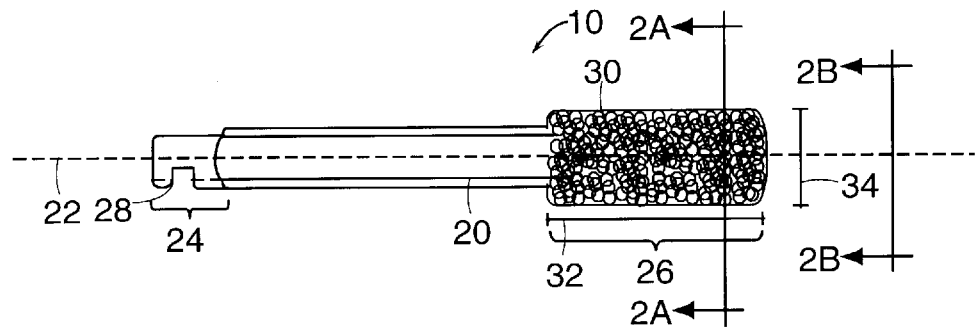
FIG. 1 is a side view of a dental debridement tool according to the invention.

Referring to FIGS. 1–5, a dental debridement tool 10 is provided for use with a rotary dental handpiece 12 to remove a surface contaminant such as a piece of dental cement 14 (not necessarily shown to scale) from a surface 16 of a tooth 18. The tool 10 includes a cylindrically shaped shaft 20 (built from metal or plastic or a combination) extending along an axis 22 and having a proximal end 24 and a distal end 26. The proximal end 24 is sized and shaped for connection to the rotary dental handpiece 12. For example, as shown, the proximal end 24 may be smaller than the shaft 20 generally. In addition, a notch 28 may be provided at the proximal end 24 to allow the tool 10 to connect to the handpiece 12.

The debridement tool 10 also includes a substantially cylindrically shaped operative tip 30 being carried at the distal end 26 of the shaft 20. The operative tip 30 has a length 32 parallel to the axis 22 and a width (i.e., diameter) 34 perpendicular to the axis 22. The length 32 is at most 8.0 millimeters (preferably 3.0 to 6.0 millimeters) and the width 34 is at most 4.0 millimeters (preferably 1.5 to 2.5 millimeters).

The operative tip 30 includes an abrasive composition of matter (to be described below) being sufficiently abrasive to remove the pieces of dental cement 14 from the surface 16 of the tooth 18 and also being insufficiently abrasive to damage the surface 16 of the tooth. Examples of materials used as such dental cement 14 include a Eugenol® formulation such as Kerr® Tempbond®; calcium hydroxide formulations such as Caulk® Dycal® and Kerr® Life®; polycarboxylate cements; glass ionomers; resin luting cements; and zinc phosphate cements.

Figure 3:
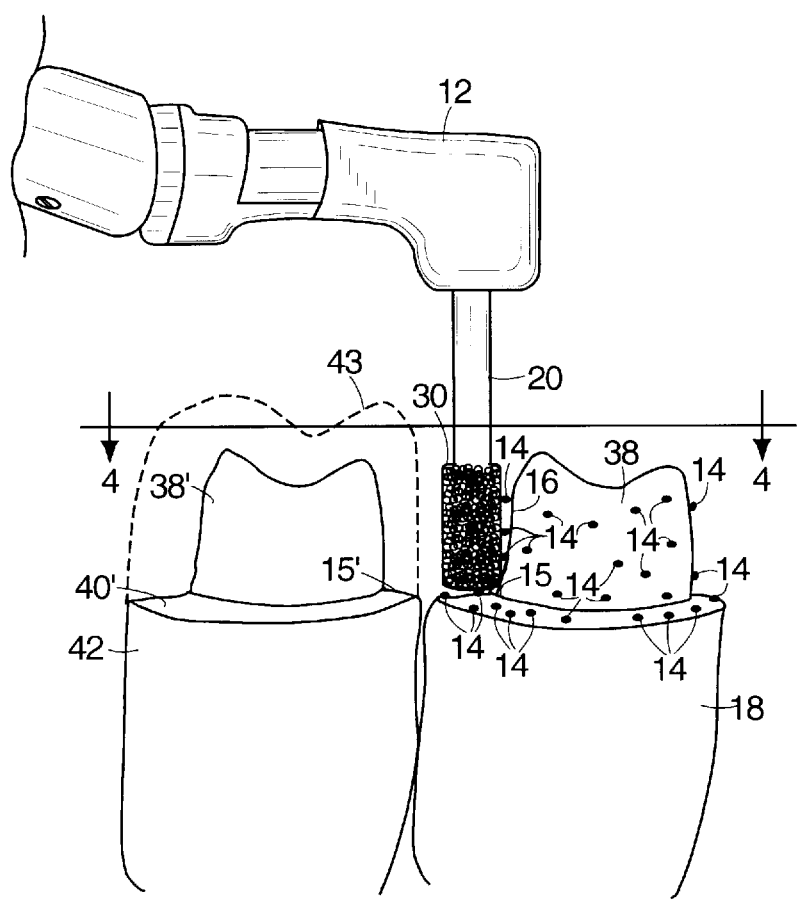
FIG. 3 is a side view of an application of the tool of FIG. 1.
Figure 4:
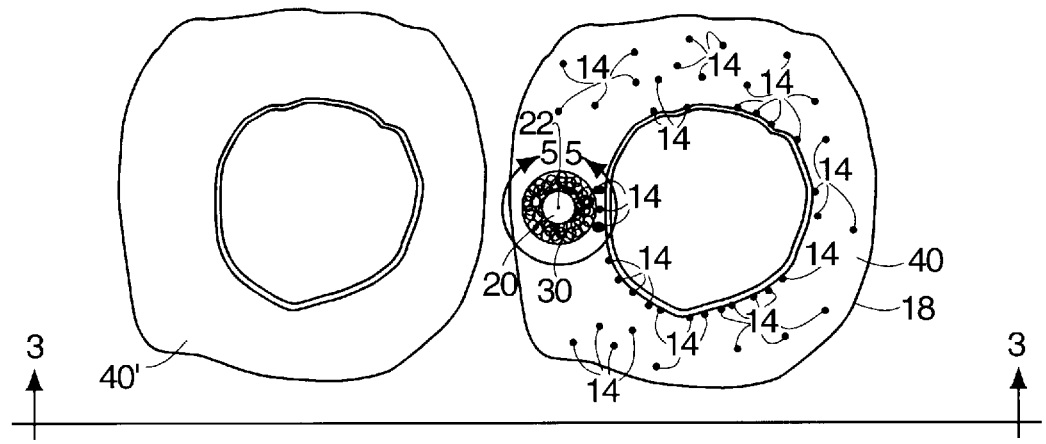
FIG. 4 is a top view of the application of FIG. 3.

Referring to FIGS. 3–6, a dentist (not shown) uses the tool 10 to debride the tooth surface 16. Such debridement is necessary after the dentist has prepared the tooth 18 for receiving permanent restorative dental material (not shown) such as a crown. The dentist prepares the tooth 18 by drilling (i.e., sculpting) the tooth 18 into the shape shown and then temporarily covering the tooth 18 with temporary restorative material (not shown). After drilling, the tooth 18 appears as shown, having a substantially vertical wall 38 (FIG. 3) and a substantially horizontal gingival shoulder 40 (FIGS. 3, 4). (For clarity, FIG. 3 also shows a corresponding wall 38' and a corresponding shoulder 40' of an adjacent drilled tooth 42.) Both the wall 38 and the shoulder 40 curve around in a substantially circular fashion. The tooth surface 16 covers both the walls 38 and the shoulder 40.

Figure 5:
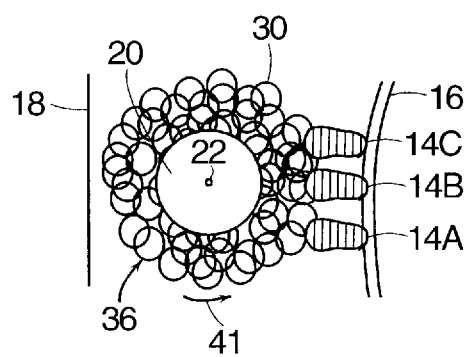
FIG. 5 is an enlarged view of the tool of FIG. 4.

The dental handpiece 12 causes the operative tip to rotate as shown in FIG. 5. Preferably, the operative tip rotates at a rotation speed between 300 and 5,000 revolutions per minute. The width 34 of the operative tip 30 allows the dentist to place the operative tip 30 as shown in FIG. 3, between the tooth 18 and the adjacent tooth 42. Such placement is possible even if the adjacent tooth 42 is not drilled (i.e., is a fully-contoured tooth), as shown by a dashed line 43. Such rotation and placement provides simultaneous debridement of the wall 38 and the shoulder 40, because the operative tip 30 brushes against the wall 38 and the shoulder 40 simultaneously.

Figure 2A:
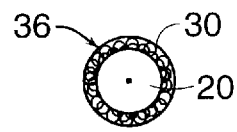
FIG. 2A is a cross-sectional view of the tool of FIG. 1.
Figure 2B:
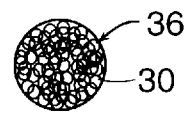
FIG. 2B is a frontal view of the tool of FIG. 1.
Figure 6:
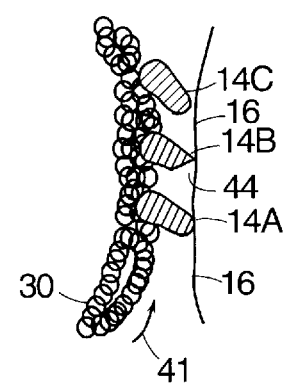
FIG. 6 is an enlarged view of the tool of FIG. 5.

Referring now to FIGS. 5 and 6 in particular, the operation of the operative tip 30 is described in relation to first, second, and third pieces 14A–C of dental cement 14. An outer surface 36 of the operative tip 30 continuously brushes across the pieces 14A–C as the operative tip 30 rotates. (As shown in FIG. 2B, the outer surface 36 preferably completely covers the most distal portion of the operative tip 30 so that the shaft 20 is not visible from a frontal view.) The outer surface 36 catches the pieces 14A–C of dental cement 14, imparting sufficient force to urge the pieces 14A–C away from the tooth surface 16. First, as shown in FIG. 6 by the first piece 14A, each piece 14A–C is deformed in the direction 41 of rotation. Preferably, the outer surface 36 is sufficiently compressible to allow each piece 14A–C to be gripped by and to become embedded in the outer surface 36. Next, as shown in FIG. 6 by the second piece 14B, the outer surface 36 causes a break 44 between each piece 14A–C and the tooth surface 16. Finally, as shown in FIG. 6 by the third piece 14C, each piece 14A–C is completely physically disconnected from the tooth surface 16, i.e., is sheared off the tooth surface 16.

Figure 7:
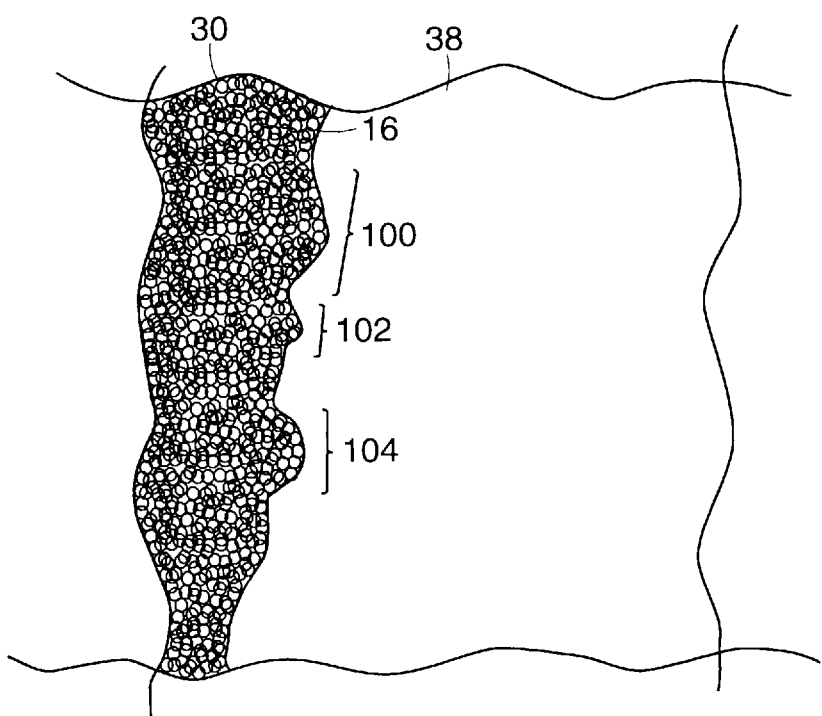
FIG. 7 is an enlarged view of the application of FIG. 3.

Furthermore, the operative tip 30 is preferably sufficiently compressible to conform substantially to the shape of the tooth 18 during operation. As shown in FIG. 7 (which is an enlarged view, not necessarily to scale, of the tooth surface 16), such compressibility preferably allows the operative tip 30 to remain in intimate contact with the tooth surface 16 despite irregularities such as contours 100, 102, 104 in the tooth surface 16. The operative tip 30 fills the contours 100, 102, 104 so that the operative tip 30 can reach any dental cement 14 (not shown) disposed in the contours 100, 102, 104. In another example (now referring back to FIG. 3), the operative tip 30 is preferably able to remove dental cement 14 disposed at a point 15 where the wall 38 and the shoulder 40 meet (corresponding to a point 15' where wall 38' and shoulder 40' meet on the adjacent tooth 42).

In addition, the operative tip's abrasive composition is preferably a non-woven abrasive material such as but not limited to 3M™ Scotch-Brite™ Cleaning Pad mineral-impregnated material. The abrasive material may include polystyrene, polyethylene, polyester, acrylic, or silicone. The abrasive material is produced by blowmolding a molten polymer and then compressing the polymer into sheets. After the abrasive material is shaped into the operative tip 30, the operative tip 30 is preferably bonded to the shaft 20 by a means known in the art, e.g., using a glue such as a thermoplastic glue or a chemically interactive glue.

Alternatively, a foam polymer may be used to produce the abrasive composition. The foam polymer is preferably impregnated with abrasive particles provided by an abrasive powder such as flour of pumice, mica, diamonds, ceramics, aluminum oxide, tin oxide, or silicone oxide.

Furthermore, the abrasive composition preferably has sufficient porosity to carry a disinfecting agent (e.g., a chemoactive liquid) for disinfecting purposes. The disinfecting agent is applied to the tooth surface 16 as the operative tip 30 is rotated for debriding the tooth surface 16, providing simultaneous debridement and disinfecting. Alternatively, the porous abrasive composition carries water to assist in the debridement of the tooth surface 16.

In particular, the abrasive composition may include a material identified as M72 "Grey Nowax" available from Loren Products (a division of Ivax Industries Inc.) of Lawrence, Mass. This material includes a fiber being a 6 dpf Polyester (PET), heavily needled, and has a binder/coating being a water-based latex such as an acrylic supplied by Rohm and Haas Company or a styrene acrylic supplied by B. F. Key. The binder/coating is externally crosslinked with a methylated melamine resin supplied by, e.g., Monsanto Company. The abrasive composition may also include an inorganic substance such as an industrial talc supplied by R. T. Vanderbilt Company, Inc., and pigmentation achieved using titanium dioxide supplied by, e.g., Truesdale Company of Brighton, Mass. Further, minor additives may also be included in the abrasive composition to improve wetting for an even distribution of the binder/coating and to act as a chemical catalyst.

Alternatively, the abrasive composition may include a material identified as M71, which available from the same source as M72 and which has the same characteristics as M72 except that M71 has a white color.

Other embodiments are within the scope of the following claims. For example, the tooth surface may not be an outward-facing surface such as the tooth surface 16 described above. The operative tip 30 may debride an inward-facing surface, such as a surface of a dental cavity drilled out for filling with a white filling such as a porcelain inlay or a composite quartz resin containing a light sensitive agent.

Furthermore, the operative tip 30 may be used to remove surface stains from teeth. For example, stain specks may be removed from grooves in a tooth's biting surface to prevent the specks from showing up on an image produced by an intra-oral camera.

Also, the operative tip 30 need not be cylindrical. The operative tip 30 may have a convex or concave shape. For example, the operative tip 30 may have a ball shape.

What is claimed is:

1. A dental tool for use with a rotary dental handpiece to remove a surface contaminant from a surface of a tooth, the tool comprising:

a shaft extending along an axis and having a proximal end and a distal end, the proximal end being sized and shaped for connection to the rotary dental handpiece; and an operative tip being carried at the distal end of the shaft and having a length parallel to the axis, the length being at most 8.0 millimeters, the operative tip being no wider than 4.0 millimeters at any point along the length, the operative tip being operably compressible during removal of the surface contaminant, the operative tip having an outer surface comprising a catching material for catching the surface contaminant and urging the surface contaminant away from the surface of the tooth, the catching material being configured to impart a force when the tool is rotated by the rotary dental handpiece, the force being sufficient to cause a break between the surface containment and the surface of the tooth and being insufficient to remove tooth material from the surface of the tooth, the catching material being sufficiently porous to carry a disinfecting liquid and to deliver the disinfecting liquid to the surface of the tooth while catching the surface contaminant.

2. The tool of claim 1, wherein the force is sufficient to remove dental cement from the surface of the tooth.

3. The tool of claim 2, wherein the catching material comprises a material selected from the group consisting of polystyrene, polyethylene, polyester, acrylic, and silicone.

4. The tool of claim 2, wherein the catching material comprises an abrasive powder.

5. The tool of claim 4, wherein the abrasive powder comprises a material selected from the group consisting of pumice, mica, diamond, talc, aluminum oxide, tin oxide, and silicone oxide.

6. The tool of claim 4 wherein the abrasive powder comprises a ceramic material.

7. The tool of claim 1 wherein the operative tip has a substantially cylindrical shape.

8. A dental tool for use with a rotary dental handpiece to remove a surface contaminant from a surface of a tooth, the tool comprising:

a shaft extending along an axis and having a proximal end and a distal end, the proximal end being sized and shaped for connection to the rotary dental handpiece; and an operative tip being carried at the distal end of the shaft and having a length parallel to the axis, the length being at most 8.0 millimeters, the operative tip being no wider than 4.0 millimeters at any point along the length, the operative tip configured for rotation about the axis at a rotation speed being between 300 and 5,000 revolutions per minute, the operative tip having an outer surface comprising a catching material for catching the surface contaminant and urging the surface contaminant away from the surface of the tooth, the catching material being configured to impart a force when the tool is rotated by the rotary dental handpiece, the force being sufficient to cause a break between the surface contaminant and the surface of the tooth and being insufficient to remove tooth material from the surface of the tooth, the catching material being sufficiently porous to carry a disinfecting liquid and to deliver the disinfecting liquid to the surface of the tooth while catching the surface contaminant.

9. The tool of claim 8, wherein the catching material comprises a material selected from the group consisting of polystyrene, polyethylene, polyester, acrylic, and silicone.

10. The tool of claim 8, wherein the catching material comprises an abrasive powder.

11. A dental tool for use with a rotary dental handpiece to remove a surface contaminant from a surface of a tooth, the tool comprising:

a shaft extending along an axis and having a proximal end and a distal end, the proximal end being sized and shaped for connection to the rotary dental handpiece; and an operative tip being carried at the distal end of the shaft and having a length parallel to the axis, the length being at most 8.0 millimeters, the operative tip being no wider than 4.0 millimeters at any point along the length, the operative tip comprising heavily needled polyester fiber with a water-based latex binder/coating externally crosslinked with a resin.

12. The tool of claim 11 wherein the operative tip further comprises an industrial talc.

13. A method for debriding a surface of a tooth, the method comprising using a tool comprising:

a shaft extending along an axis and having a proximal end and a distal end, the proximal end being sized and shaped for connection to a rotary dental handpiece; and an operative tip being carried at the distal end of the shaft and having a length parallel to the axis, the length being at most 8.0 millimeters, the operative tip being no wider than 4.0 millimeters at any point along the length, the operative tip being operably compressible during removal of a surface contaminant from the surface of the tooth, the operative tip having an outer surface comprising a catching material for catching the surface contaminant and urging tbe surface contaminant away from the surface of the tooth, the catching material being configured to impart a force when the tool is rotated by the rotary dental handpiece, the force being sufficient to cause a break between the surface contaminant and the surface of the tooth and being insufficient to remove tooth material from the surface of the tooth, the catching material being sufficiently porous to carry a disinfecting liquid and to deliver the disinfecting liquid to the surface of the tooth while catching the surface contaminant.

14. The method of claim 13 wherein the tooth surface is a outward-facing surface of the tooth.

15. The method of claim 13 wherein the tooth surface is an inward-facing surface of the tooth.

16. A method for debriding a surface of a tooth, the method comprising using a tool comprising a shaft extending along an axis and having a proximal end and a distal end, the proximal end being sized and shaped for connection to a rotary dental handpiece; and an operative tip being carried at the distal end of the shaft and having a length parallel to the axis, the length being at most 8.0 millimeters, the operative tip being no wider than 4.0 millimeters at any point along the length, the operative tip configured for rotation about the axis at a rotation speed being between 300 and 5,000 revolutions per minute, the operative tip having an outer surface comprising a catching material for catching a surface contaminant and urging the surface contaminant away from the surface of the tooth, the catching material being configured to impart a force when the tool is rotated by the rotary dental handpiece, the force being sufficient to cause a break between the surface contaminant and the surface of the tooth and being insufficient to remove tooth material from the surface of the tooth, the catching material being sufficiently porous to carry a disinfecting liquid and to deliver the disinfecting liquid to the surface of the tooth while catching the surface contaminant.

17. A dental tool comprising:

at a proximal end of the tool, an element configured to connect to a rotary dental handpiece; and at a distal end of the tool, an operative tip having a length along an axis of rotation, the length being at most 8.0 millimeters, the operative tip being no wider than 4.0 millimeters at any point along the length, the operative tip being operably compressible during removal of a surface contaminant from a surface of a tooth, the operative tip having an outer surface comprising a catching material for catching the surface contaminant and urging the surface contaminant away from the surface of the tooth, the catching material being configured to impart a force when the tool is rotated by the rotary dental handpiece, the force being sufficient to cause a break between the surface contaminant and the surface of the tooth and being insufficient to remove tooth material from the surface of the tooth, the catching material being sufficiently porous to carry a disinfecting liquid and to deliver the disinfecting liquid to the surface of the tooth while catching the surface contaminant.

18. A dental tool comprising:

at a proximal end of the tool, an element configured to connect to a rotary dental handpiece; and at a distal end of the tool, an operative tip having a length along an axis of rotation, the length being at most 8.0 millimeters, the operative tip being no wider than 4.0 millimeters at any point along the length, the operative tip being operably compressible during removal of the surface contaminant, the operative tip comprising an abrasive composition of matter that comprises heavily needled polyester fiber with a water-based latex binder/coating externally crosslinked with a resin.

* * * * *